United States Patent [19]

Bergstresser et al.

[11] Patent Number: 5,730,729
[45] Date of Patent: Mar. 24, 1998

[54] SELF-TAPPING PLUNGER ROD FOR CARTRIDGE NEEDLE UNIT

[75] Inventors: William A. Bergstresser, Prattsburgh; Mark A. Stiehl, Rochester, both of N.Y.

[73] Assignee: Sanofi Winthrop Inc., New York, N.Y.

[21] Appl. No.: 461,609

[22] Filed: Jun. 5, 1995

Related U.S. Application Data

[63] Continuation of Ser. No. 128,933, Sep. 29, 1993, abandoned.

[51] Int. Cl.⁶ .................................................. A61M 5/315
[52] U.S. Cl. .................................. 604/228; 604/218
[58] Field of Search .................................. 604/181, 187,
604/228, 218, 232, 234, 240, 241, 224,
221, 219; 411/418, 419, 420, 421, 422,
427, 918, 919, DIG. 1

[56] References Cited

U.S. PATENT DOCUMENTS

| | | |
|---|---|---|
| 939,693 | 11/1909 | Holtzmann . |
| 1,110,189 | 9/1914 | Dodge . |
| 1,552,181 | 9/1925 | Solomon et al. . |
| 2,550,394 | 4/1951 | Young et al. . |
| 2,555,878 | 6/1951 | Drabicki . |
| 2,661,740 | 12/1953 | Hickey . |
| 2,753,867 | 7/1956 | Goldberg . |
| 2,832,340 | 4/1958 | Dann et al. ............ 604/228 |
| 2,904,043 | 9/1959 | Friedman . |
| 3,080,866 | 3/1963 | Friedman . |
| 3,091,240 | 5/1963 | McConnaughey et al. . |
| 3,128,765 | 4/1964 | Tint ............ 604/228 |
| 3,224,445 | 12/1965 | Melott . |
| 3,548,824 | 12/1970 | Carr . |
| 3,577,980 | 5/1971 | Cohen . |
| 3,742,949 | 7/1973 | Hill ............ 604/228 |
| 3,825,002 | 7/1974 | Paige ............ 604/241 |
| 4,031,890 | 6/1977 | Homan . |
| 4,701,165 | 10/1987 | DeHaitre . |
| 4,752,291 | 6/1988 | Magrath ............ 604/241 |
| 4,770,560 | 9/1988 | Ott ............ 411/418 |
| 4,931,043 | 6/1990 | Ray et al. . |
| 5,112,316 | 5/1992 | Venturini ............ 604/198 |

FOREIGN PATENT DOCUMENTS

0142910  6/1990  Japan .................................. 411/418

*Primary Examiner*—C. Fred Rosenbaum
*Assistant Examiner*—Ronald K. Stright, Jr.
*Attorney, Agent, or Firm*—William J. Davis; Paul E. Dupont

[57] ABSTRACT

An article of manufacture adapted to be connected to a male thread comprises an exterior surface, a cavity opening away from the exterior surface and defining an interior surface, and a plurality of ribs disposed on the interior surface extending longitudinally away from the exterior surface. The article can be connected to the male thread by threading the cavity onto the male thread. It is a particular advantage that the article of this invention, unlike prior art female threaded articles, can be prepared by conventional simple injection molding techniques not requiring an unscrewing step. In one preferred embodiment, the article is a plunger rod intended to be connected to the male threaded post of a plunger of an associated cartridge-needle unit to form a syringe assembly.

5 Claims, 3 Drawing Sheets

5,730,729

SELF-TAPPING PLUNGER ROD FOR CARTRIDGE NEEDLE UNIT

This is a Continuation of prior application Ser. No. 08/128,933 filed Sep. 29, 1993 now abandoned.

BACKGROUND OF THE INVENTION

1. Field of the Invention

This invention relates to articles intended to be connected to a male thread. In one particular embodiment, this invention relates to a plunger rod intended to be connected to the male threaded post of a plunger of an associated cartridge-needle unit to form a syringe assembly.

2. Description of the Prior Art

It is well known to manufacture articles, particularly plastic articles, by injection molding techniques. Such techniques are in widespread commercial use. In a conventional simple injection molding process, two halves of a mold get clamped together under pressure. The molds form a cavity having the desired shape of the article to be fabricated. A molten fluid, e.g., molten plastic, is then injected through a tiny orifice or gate into the cavity until the cavity is filled. Next, the article is permitted to solidify during a so-called cure phase. After curing, the molds are separated and the article is ejected, usually with the assistance of an ejection device. This completes a cycle which is then repeated, desirably at high speeds. Short cycle times are highly desired primarily from the standpoint of the economies of manufacturing.

Such injection molding techniques work well for many articles. However, articles of particular shapes can pose substantial or even insurmountable problems with respect to manufacture by injection molding. For example, articles intended to be threaded onto a male thread and containing internal threads, i.e., female threads, require that the article be unscrewed from the mold. In practice, this is typically accomplished by unscrewing the mold from the article in order to remove the article from the mold without damage to the threads. Although unscrewing mechanisms for injection molds are known, they are extremely capital intensive, costly to maintain, and add significantly to the complexity of the injection molding process. Perhaps more significantly, the unscrewing step is relatively time consuming, resulting in lengthy cycle times, which leads to manufacturing diseconomies.

It would be desirable to be able to provide articles which, like conventional internal female threaded articles, can be connected to male threads and which can be prepared in a simple injection molding process not requiring a complex unscrewing step or long cycle time.

SUMMARY OF THE INVENTION

We have discovered that injection molded articles containing internal, i.e., female threads, which heretofore required a step in which the article is unscrewed from the mold, can be designed such that they can be easily and economically prepared by conventional simple injection molding techniques not requiring a capital intensive, cycle-extending unscrewing step.

More specifically, in accordance with this invention, there is provided an article of manufacture adapted to be connected to a male thread, such article comprising a distal portion comprising a distal exterior surface, a cavity disposed within the distal portion of said article opening away from the exterior surface and defining at least one interior surface, and a plurality of ribs disposed on the interior surface extending substantially longitudinally away from the exterior surface. The article can be connected to the male thread by threading the cavity onto the male thread.

In a preferred embodiment of this invention, the above-described article is a plunger rod intended to be connected to the male threaded post of a plunger of an associated cartridge-needle unit to form a syringe assembly.

It is a particularly advantageous feature of this invention that there is provided an article which can be connected to a male thread and which can be prepared by conventional simple injection molding techniques not requiring a complex unscrewing step or long cycle time.

Other advantages will become readily apparent upon reference to the following description of preferred embodiments when read in light of the accompanying drawings.

DESCRIPTION OF PREFERRED EMBODIMENTS

This invention is based at least partly on the discovery that articles intended to be threaded onto a male thread, i.e., female threaded articles, can be redesigned such that the article can be prepared in a conventional simple injection molding process not requiring a capital intensive, cycle-extending, unscrewing step. The invention is described herein primarily in connection with a currently preferred embodiment, i.e., with respect to a plunger rod intended to be connected to the male threaded post of a plunger of an associated cartridge-needle unit. However, the invention also finds utility in numerous other embodiments, particularly those wherein an injection molded article is intended to be connected onto a male thread.

Figure 7:
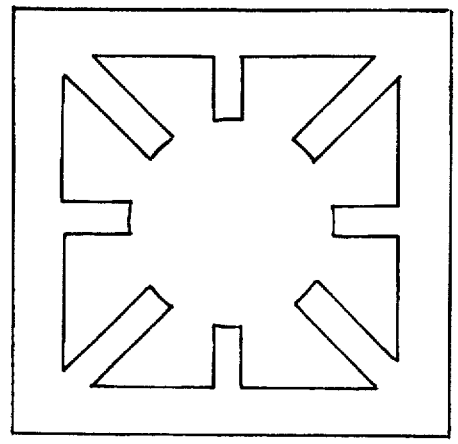
FIG. 7 is a bottom view of the distal end of another embodiment of the plunger of this invention.

The article of this invention, preferably a plunger rod 10 as depicted in FIGS. 1–5, comprises a distal portion comprising a distal exterior surface 12 on the distal end of the plunger and a cavity within the distal portion of the rod 14 opening away from the exterior surface. The cavity defines an interior surface 16. At least one interior surface is present. However, as indicated by FIG. 7, more than one interior surface can be present. Disposed on the interior surface of the cavity are a plurality of ribs 18. The ribs extend substantially longitudinally and axially away from the exterior surface. Ribs extending radially around the interior surface of the cavity, like conventional female threads, do not provide all of the advantages of this invention. Such radial ribs, of any significant height, can not be manufactured in a simple injection molding process. The longitudinal ribs in accordance with this invention facilitate the use of a simple injection molding process by enabling the article to be removed, i.e., backed out or ejected from, the mold without a complex unscrewing step.

Figure 6:
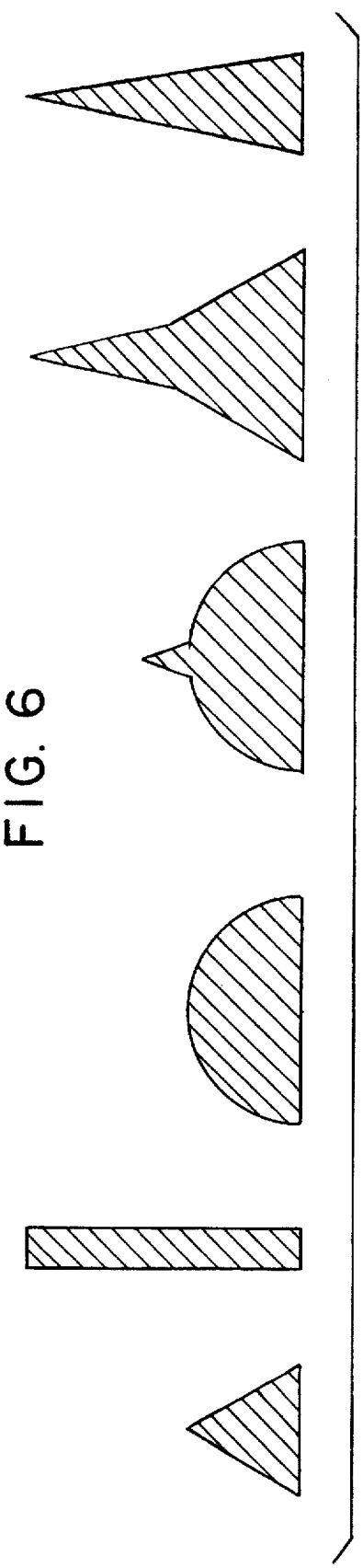
FIG. 6 is a cross-sectional view of various ribs in accordance with this invention.

In preferred embodiments, the ribs are V-shaped, i.e., triangular in cross section. Applicants have discovered that this shape provides high retention capability, i.e., a good threaded connection between the article and the male thread upon threading. However, other rib shapes, such as, for example, rectangular ribs, semicircular ribs, and the like, such as depicted in cross section in FIG. 6, are also operable. In preferred embodiments, the article comprises from two to about fourteen, more preferably from three to twelve ribs.

The article of this invention and male threaded post can be fabricated of any suitable materials including metals and plastics. However, it is a particular advantage that the article can be fabricated of rigid plastic using known simple precision injection molding techniques. Suitable plastics include polyethylene, polypropylene, polystyrene, polycarbonates, polyester, ABS (clear or opaque), nylon, acetals such as DERLIN®, and the like. Suitable metals include aluminum, brass, copper, and steel. It is believed that the article must be fabricated of a material which is more ductile than the material of which the male thread is fabricated, to enable the ribs to conform to the shape of the male threads, thus providing connecting engagement between the article and the male thread upon threading. While the applicants do not wish to be bound by theoretical mechanisms, it is believed that the threading motion causes thread-like deformations to form in the ribs.

Figure 1:
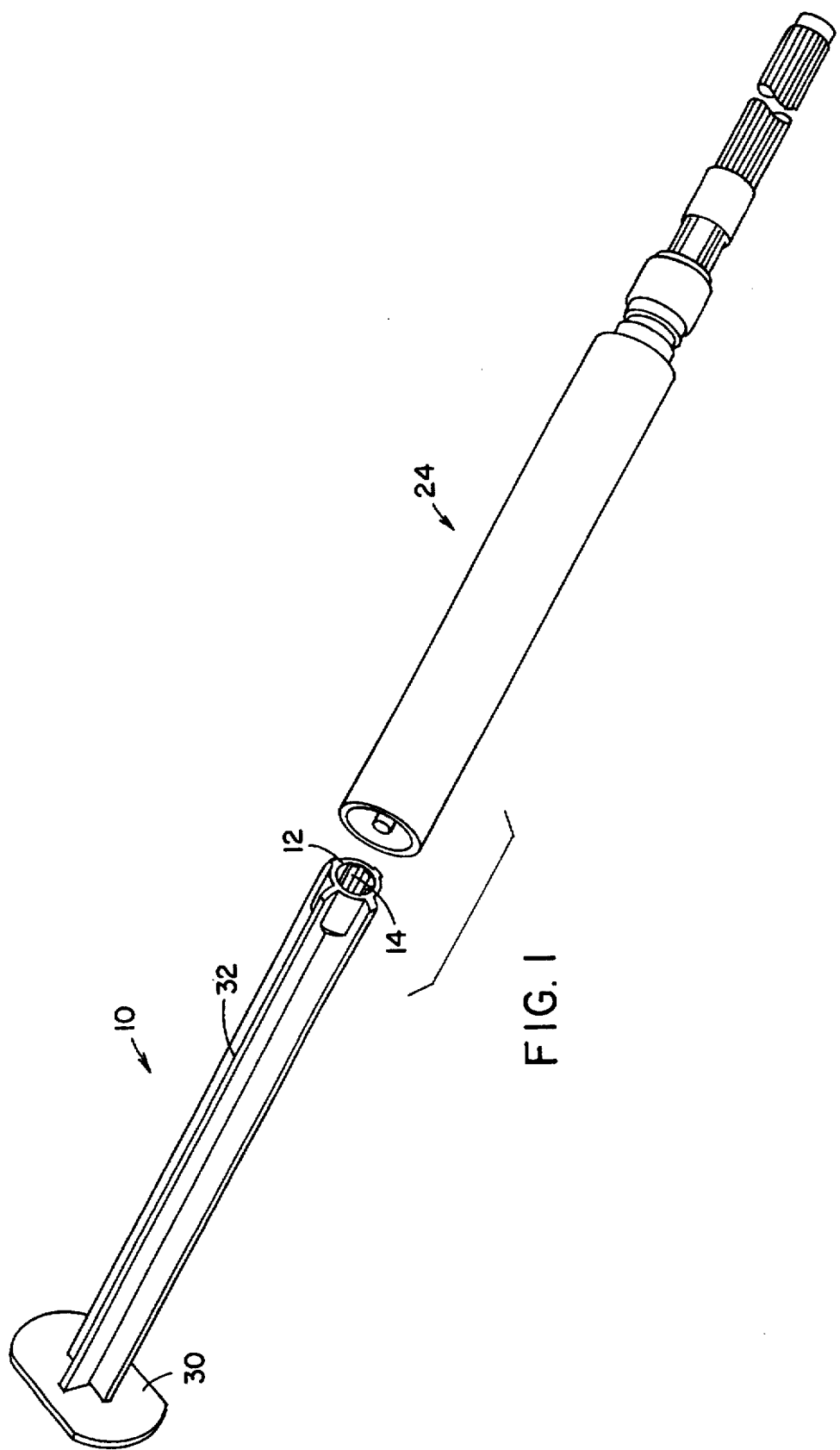
FIG. 1 is an exploded perspective showing views of a preferred embodiment of this invention, i.e., a plunger rod and an associated cartridge-needle unit.
Figure 3:
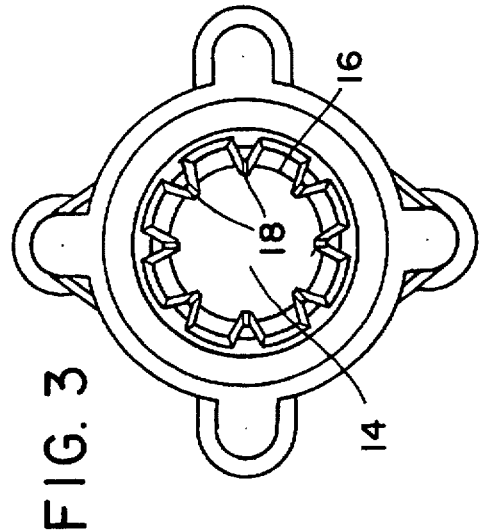
FIG. 3 is a bottom view of the distal end of the plunger illustrating a plurality of V-shaped ribs.
Figure 5:
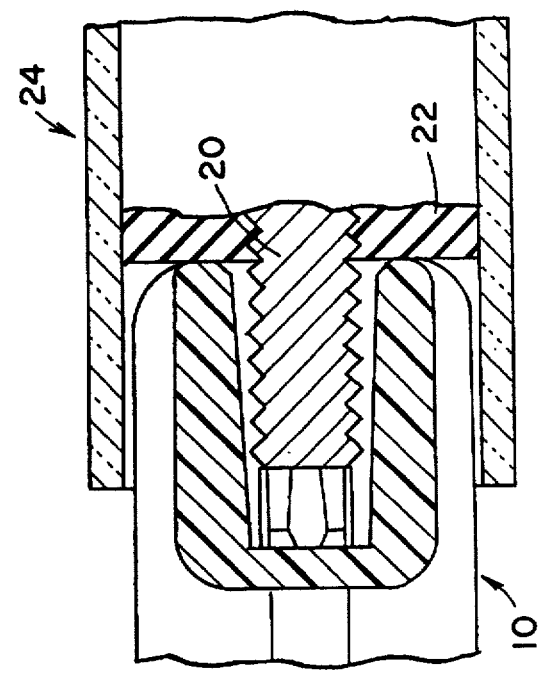
FIGS. 4 and 5 are cross-sectional views illustrating a plunger rod before and after connection to the male threaded post of a plunger of a cartridge-needle unit.
Figure 2:
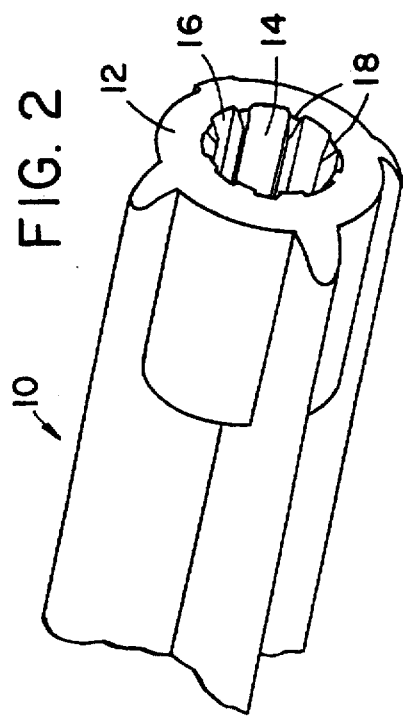
FIG. 2 is a perspective view of the distal portion of the plunger rod depicted in FIG. 1.
Figure 4:
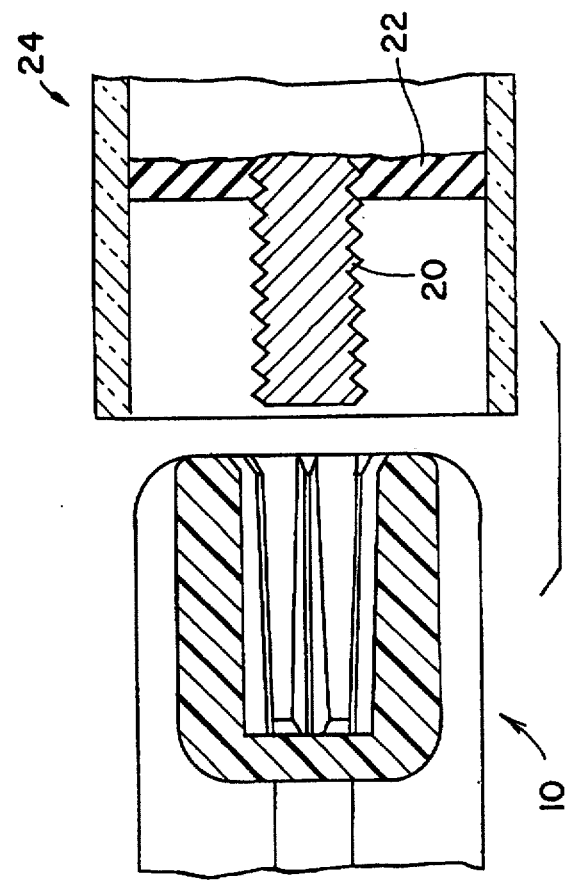

In use, the article of this invention can be threaded onto the male thread using a conventional threading motion. For example, as illustrated in FIGS. 4 and 5, a plunger rod in accordance with this invention can be threaded onto the male threaded post 20 of plunger 22 of associated cartridge-needle unit 24 using a conventional threading technique, thus providing connecting engagement.

Medicament-containing cartridge needle units are well known in the art and in widespread commercial use. Such cartridges conventionally feature a cylindrical body closed at the proximal end with a flexible plunger slidable within the bore of the cartridge and closed at the distal necked-down end with a septum secured to the cartridge by a crimped-on aluminum collar. The necked-down distal end conventionally is fitted with a needle hub/needle/needle guard assembly. Such cartridge-needle units are available from Sanofi Winthrop Pharmaceuticals under the Carpuject® trademark. In a preferred embodiment the prefilled cartridge-needle unit can be of a conventional design and can include a hollow, transparent body prefilled with a supply of fluid medication or the like. Such cartridge-needle units currently are in widespread commercial use. The cartridge can include a head portion and a cylindrical body which are co-extensively joined together at a relatively narrow neck. A metallic end cap can cover the sealed septum which extends across the distal end of the cartridge to prevent contamination and leakage of the fluid contents. The plunger is sized to be received in and slidable axially and reciprocally through the interior of the cartridge. The necked-down distal end of the cartridge-needle unit can be fitted with a needle/hub/needle/needle guard assembly. The needle hub can be attached to the cartridge by snapping the sleeve portion over the distal end of the cartridge to engage the metallic end cap.

In a particularly preferred embodiment of this invention, the plunger rod features a plunger thumb pad or actuation button 30 and fins 32 enabling the plunger rod to be snap attached to a retention feature on the body of a holder. Such a retention feature and a preferred holder for use with this invention are described in commonly-assigned U.S. patent application Ser. No. 08/129,878 entitled DISPOSABLE HOLDER FOR PREFILLED CARTRIDGE-NEEDLE UNIT, filed on Sep. 29, 1993, the disclosure of which is hereby incorporated by reference in its entirety.

As noted, it is a particular advantage that articles of this invention can be prepared by simple injection molding techniques not requiring an unscrewing step. Applicants have found that this creates a significant competitive advantage from the standpoint of the economies of manufacturing. More specifically, the applicants have found that articles can be prepared in accordance with this invention by simple injection molding techniques at substantially reduced manufacturing costs, including capital costs, and with substantially reduced cycle times, compared to articles prepared by injection molding techniques requiring an unscrewing step.

The invention has been described in detail with particular reference to certain preferred embodiments thereof, but it will be understood that variations and modifications can be effected within the spirit and scope of the invention.

What is claimed is:

1. In combination, a plunger rod and a cartridge-needle unit containing a plunger containing a male threaded post, wherein said plunger rod is adapted to be connected to said male threaded post of said plunger of said cartridge-needle unit, said cartridge-needle unit comprising:
    a needle,
    a hub for said needle, and
    a hollow cylindrical cartridge having a proximal end and a distal end,
    said plunger being slidable within said cartridge, said cartridge being closed at the distal end with a septum secured to the cartridge by an aluminum collar, and said needle hub being attached to the distal end of said cartridge: and said plunger rod comprising:
    a distal portion comprising a distal exterior surface;
    a cavity disposed within the distal portion of said rod opening away from said exterior surface and defining at least one interior surface; and
    a plurality of ribs disposed on said interior surface extending substantially longitudinally away from said exterior surface;
    whereby said plunger rod can be connected to said plunger by threading said cavity onto said post.

2. The plunger rod cartridge-needle unit combination of claim 1 wherein said ribs are V-shaped.

3. The plunger rod cartridge-needle unit combination of claim 1 wherein said plunger rod comprises from three to twelve of said ribs.

4. The plunger rod cartridge-needle unit combination of claim 1 wherein said plunger rod is fabricated of plastic.

5. The plunger rod cartridge-needle unit combination of claim 1 wherein said plunger rod is fabricated of a material which is more ductile than said male threaded post.

* * * * *